(12) United States Patent
Freifeld et al.

(10) Patent No.: US 10,005,755 B2
(45) Date of Patent: Jun. 26, 2018

(54) MOST EFFECTIVE PROCESS FOR BASE-FREE PREPARATION OF KETONE INTERMEDIATES USABLE FOR MANUFACTURE OF NEBIVOLOL

(71) Applicant: CORDON PHARMA INTERNATIONAL GmbH, Plankstadt (DE)

(72) Inventors: Ilia Freifeld, Bad Vilbel (DE); Gerhard Jas, Berlin (DE); Kurt Kesseler, Hofheim (DE); Richard Robert Dauer, Longmont, CO (US)

(73) Assignee: CORDON PHARMA INTERNATIONAL GMBH, Lankstadt (DE)

( * ) Notice: Subject to any disclaimer, the term of this patent is extended or adjusted under 35 U.S.C. 154(b) by 0 days. days.

(21) Appl. No.: 14/621,414

(22) Filed: Feb. 13, 2015

(65) Prior Publication Data
US 2015/0232441 A1 Aug. 20, 2015

(30) Foreign Application Priority Data
Feb. 14, 2014 (EP) .................... 14155299

(51) Int. Cl.
*C07D 311/58* (2006.01)
(52) U.S. Cl.
CPC .................. *C07D 311/58* (2013.01)
(58) Field of Classification Search
CPC .................................................. C07D 311/58
See application file for complete search history.

(56) References Cited

U.S. PATENT DOCUMENTS

2003/0018163 A1* 1/2003 Eggen ...................... C07K 1/08
530/333

FOREIGN PATENT DOCUMENTS

EP 1803715 7/2007
WO WO 2012/095707 7/2012

OTHER PUBLICATIONS

Oikawa, Y., "Meldrum's acid in organic synthesis. 2. A general and versatile synthesis of. beta.-keto esters." The Journal of Organic Chemistry 43.10 (1978): 2087-2088.*
Athanasellis Giorgos et al: "Novel short-step synthesis of optically active tetronic acids from chiral .alpha.-hydroxy acids mediated by 1 hydroxybenzotriazole". Synlett, Georg Thieme Verlag, DE, No. 10, 2002, pp. 1736-1738.
Montalbetti C A G N et al: "Amide bond formation and peptide coupling", Tetrahedron, Elsevier Science Publishers, Amsterdam, NL, vol. 61, No. 46, Nov. 14, 2005, pp. 10827-10852.
Han S-Y et al: Recent development of peptide coupling reagents in organic synthesis, Tetrahedron, Elsevier Science Publishers, Amsterdam, NL, vol. 60, No. 11, Mar. 8, 2004, pp. 2447-2467.

* cited by examiner

*Primary Examiner* — John M Mauro
(74) *Attorney, Agent, or Firm* — JMB Davis Ben-David

(57) ABSTRACT

The invention relates to a process for the preparation of a ketone of a general formula 1

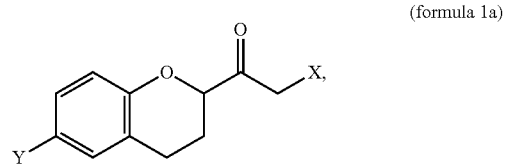

(formula 1a)

with X being Cl or Br, in particular with X being Cl, with Y being F, Cl, Br, I or H, in particular with Y being F, comprising the steps of: activation of a carboxylic acid by using a peptide coupling agent, coupling of the activated carboxylic acid with a malonic acid derivative providing a β-ketoester precursor and converting the β-ketoester precursor to the ketone of the general formula 1.

8 Claims, No Drawings

MOST EFFECTIVE PROCESS FOR BASE-FREE PREPARATION OF KETONE INTERMEDIATES USABLE FOR MANUFACTURE OF NEBIVOLOL

FIELD OF THE INVENTION

The present invention relates to an improved process for the preparation of a ketone needed for example as an intermediate for the synthesis of Nebivolol and its hydrochloride salt. The invention further relates to said ketones, the use of said ketones and methods applying said ketones.

BACKGROUND OF THE INVENTION

Nebivolol ((±)-[(S,R,R,R)±(R,S,S,S)-]-α,α'-[iminobis(methylene)]bis[6-fluoro-3,4-dihydro-2H-1-benzo-pyran-2-methanol]) and its pharmaceutically active HCl salt—as disclosed in U.S. Pat. No. 4,654,362 A and its counter EP 0145067 A2—is a potent and selective β1 adrenergic blocker used for treatment of high blood pressure. Nebivolol*HCl (nebivolol hydrochloride) is applied as a racemate and consists of the two enantiomers: d-nebivolol*HCl and l-nebivolol*HCl.

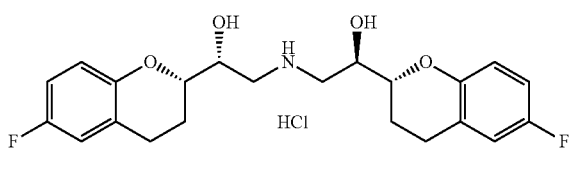

SRRR-configuration
(d-Nebivolol * HCl)

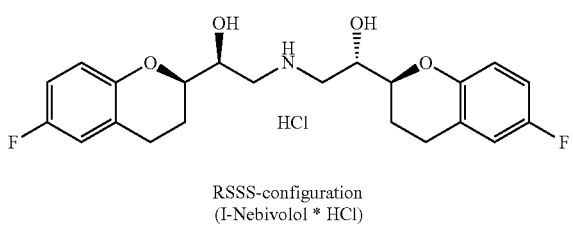

RSSS-configuration
(l-Nebivolol * HCl)

Numerous syntheses for the preparation of nebivolol hydrochloride have been disclosed, for example in U.S. Pat. No. 4,654,362 A (JANSSEN), EP 0334429 A1 (JANSSEN), WO 2004/041805 A1 (EGIS), WO 2006/016376 A1 and WO 2007/083318 A1 (HETERO DRUGS), WO 2006/025070 A2 (TORRENT), WO 2008/010022 A2 (CIMEX), WO 2008/064826 A2 and WO 2008/064827 A2 (ZACH), WO 2009/082913 A1, CN 101463024 A, WO 2010/049455 (ZACH) and WO 2010/089764 A1 (ZACH).

The challenge in each process for the manufacture of Nebivolol or its pharmaceutically active HCl salt is its unique structure as Nebivolol contains four chiral centers resulting in 16 theoretical isomers. In fact, the total number of diastereomers is reduced to only 10 due to the symmetry plane through the N atom of the molecule. As a consequence, this symmetry plane provokes similar retrosynthetic cuts in most of the published syntheses.

Not surprisingly, most of the reported processes apply the reaction of 6-fluoro-3,4-dihydro-2-oxiranyl-2H-1-benzopyran building blocks of the formula A (Scheme 1) of appropriate stereochemistry with formally ammonia, a suitably protected primary amine or azide ion.

Scheme 1: Building blocks A for the manufacture of Nebivolol

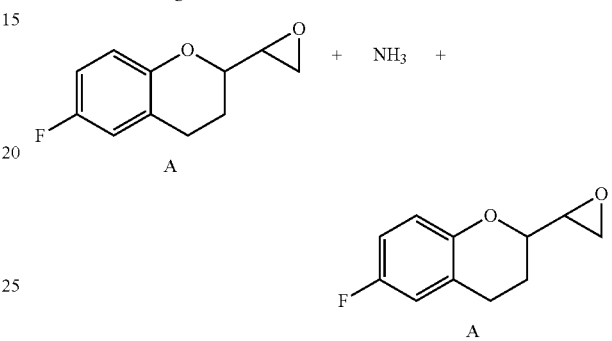

Besides other methods, suitable precursors of epoxides of formula A are chloroalcohols B

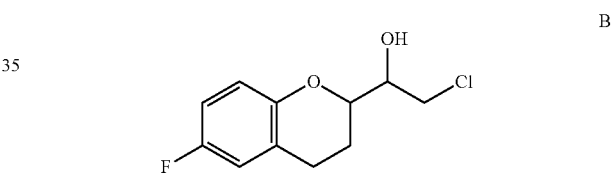

reported for the first time in EP 1803715 A1. Usually, chloroalcohols can be synthesized from chloroketones of formula C

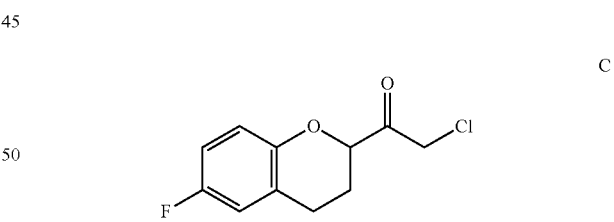

which themselves can be prepared from chromane carboxylic acids, such as 6-fluoro-chroman-2-yl-carboxylic acid, according to known techniques (see for example EP 1803715 A1, U.S. Pat. No. 7,650,575 B2).

In WO 2011/091968 A1 we disclosed a highly stereoselective approach for the synthesis of racemic nebivolol (racemic mixture of d-nebivolol and l-nebivolol) as well as for the production of the individual enantiomers d-nebivolol and l-nebivolol based on enantiomerically pure chloroketones and chloroalcohols.

The synthesis is performed according the general scheme 2.

Scheme 2: Synthesis of d- and l-nebivolol; PG is an ammine protecting group

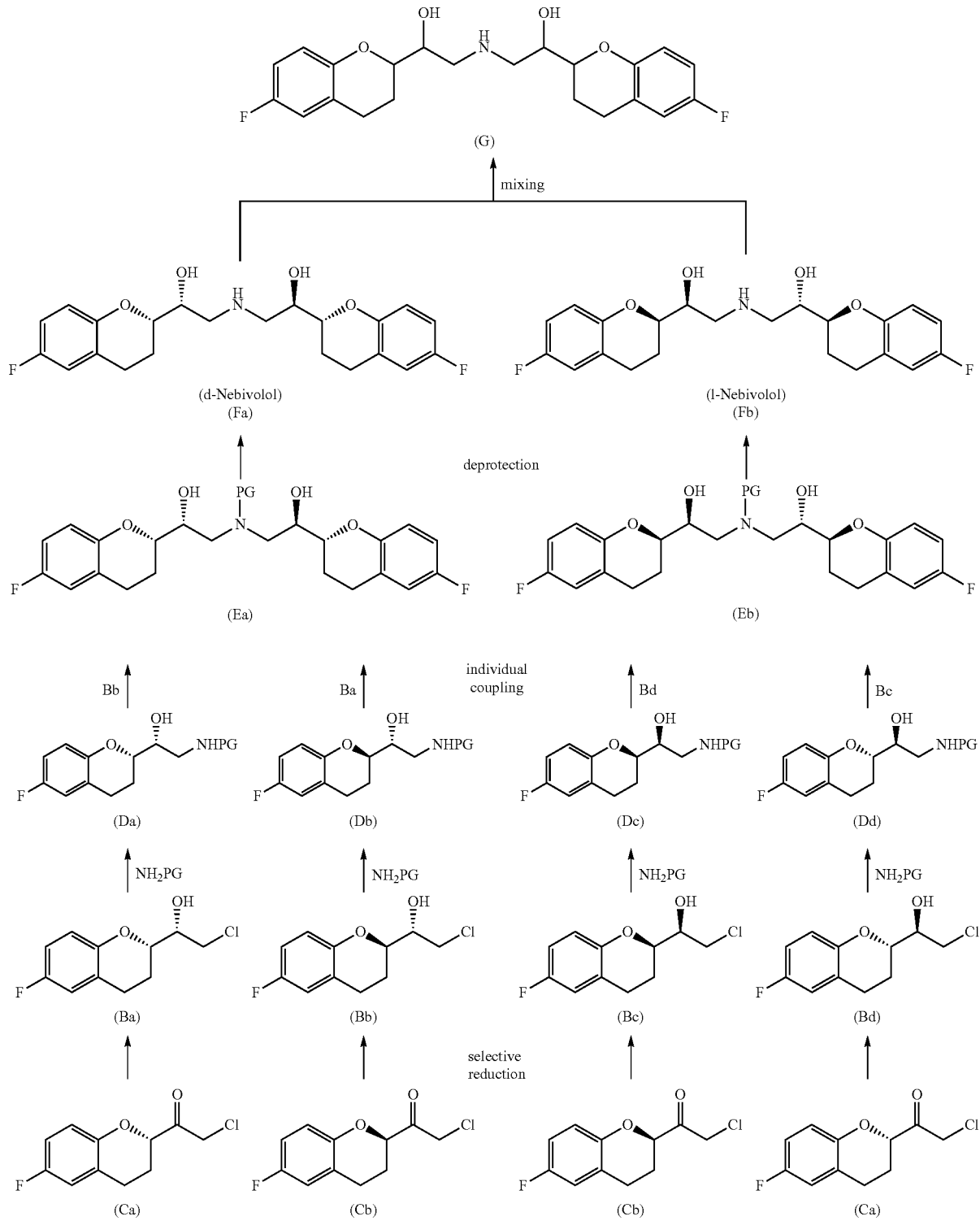

For example, d-nebivolol Fa was prepared by enzymatic reduction of 1-(2S)-(6-fluorochroman-2-yl)-2-chloroethan-1-one Ca and 1-(2R)-(6-fluorochroman-2-yl)-2-chloroethan-1-one Cb to give either the S- or the R-configurated chloroalcohol Ba or Bb. (S)-2-chloro-1-((R)-6-fluoro-3,4- dihydro-2H-chromen-2-yl)ethanol Ba was subjected to amination by treatment with sodium methoxide followed by reaction with benzylamine to give (S)-2-benzylamino-1-((R)-6-fluoro-3,4-dihydro-2H-chronnen-2-yl)ethanol Da. This underwent coupling with (R)-2-chloro-1-((R)-6-fluoro- 3,4-dihydro-2H-chronnen-2-yl)ethanol Bb followed by debenzylation to give d-nebivolol Fa. An analogue pathway applies if Bb was subjected to amination. l-Nebivolol Fb was produced in a similar way. Finally, d- and l-nebivolol (Fa and Fb) were mixed to give racemic nebivolol G which can be converted to the hydrochloride salt.

Chloroketones C can be prepared from chromane carboxylic acids according to known techniques, e.g. WO 2008010022 A2 (Cimex) describes the conversion of 6-fluoro-chromanic acid to the corresponding acid chloride, followed by reaction with Meldrum's acid with the aid of a base. We found this process unsatisfactory when starting with enantiomerically pure 6-fluoro-chromanic acid since the base induced partial isomerisation.

Other known processes for the preparation of chloroketones (for example WO 2010/034927 A1) suffer from more general aspects as the processes are based on organometallic chemistry. These processes need strong cryogenic conditions and are not feasible for industrial production from an economical point of view.

It is evident that partial isomerisation of the chloroketones C will result in lower diastereomerical purity of chloroalcohols B which leads to the formation of unwanted nebivolol diastereomers in the coupling step. This has an impact not only on the yield but also on quality of nebivolol.

The goal of the present invention is to provide a more suitable access to enantiomerically pure chloroketones which can be used in the manufacture of nebivolol and, thus, providing an economic access to Nebivolol in a high yield and high quality.

SUMMARY OF THE INVENTION

According to a first aspect, the invention relates to a process for the preparation of a ketone of a general formula 1

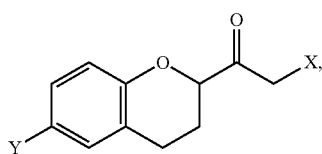

(formula 1)

with X being Cl or Br, in particular with X being Cl, with Y being F, Cl, Br, I or H, in particular with Y being F.
comprising the steps of:
a. activation of a carboxylic acid of a general formula 2

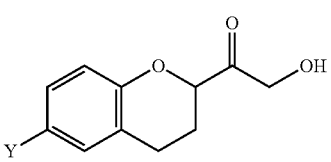

(formula 2)

by using a peptide coupling agent, with Y having the same meaning as defined above,
b. coupling of the activated carboxylic acid with a malonic acid derivative providing a β-ketoester precursor, in particular a β-ketoester precursor of the general formula 6a or 6b,

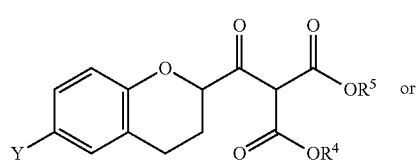

(formula 6a)

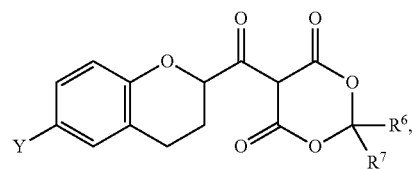

(formula 6b)

with $R^4$ being H or $C_1$ to $C_6$ alkyl, $R^5$ being H or $C_1$ to $C_6$ alkyl, $R^6$ being H or $C_1$ to $C_6$ alkyl and $R^7$ being $C_1$ to $C_6$ alkyl, or a substituted or unsubstituted phenyl, in particular $R^6$ being $C_1$ to $C_3$ alkyl and $R^7$ being $C_1$ to $C_3$ alkyl,
c. converting the β-ketoester precursor to the ketone of the general formula 1.

According to a second aspect, the invention relates to a preparation of a chiral ketone of the general formula 1a or 1b,

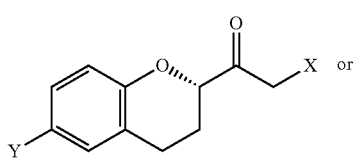

(formula 1a)

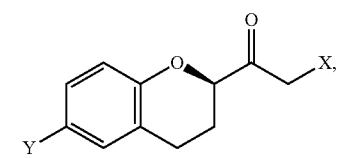

(formula 1b)

with X and Y having the same meaning as defined previously, comprising a purity of ee>98%.

According to a third aspect, the invention relates to a preparation of a chiral ketone of the general formula 1a or 1b, as defined above, producible by the process according to the first aspect of the invention, comprising a purity of ee>98%.

According to a fourth aspect, the invention relates to a use of a preparation of a chiral ketone according to the second aspect of the invention or a preparation of a chiral ketone according to the third aspect of the invention in the production of chiral alcohols of the general formula 5a to 5d,

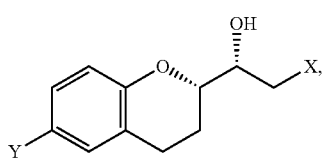

(formula 5a)

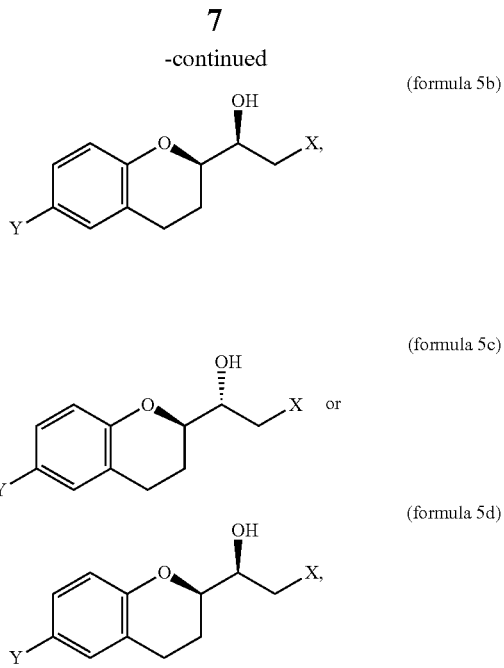

(formula 5b)

(formula 5c)

(formula 5d)

with X and Y having the same meaning as defined previously.

According to a fifth aspect, the invention relates to a use of the preparation of a chiral ketone according to the second aspect of the invention or a preparation of a chiral ketone produced according to the third aspect of the invention in the production of d-nebivolol, l-Nebivolol or a mixture of d-nebivolol and l-Nebivolol, in particular a racemic mixture of d-nebivolol and l-Nebivolol, or the hydrochloride salts thereof.

According to a sixth aspect, the invention relates to a process for the preparation of an alcohol of a general formula 5a to 5d, as defined above
comprising the steps of:
a. activation of a carboxylic acid of a general formula 2, in particular of the formula 2a or 2b, by using a peptide coupling agent, with formula 2, 2a or 2b having the same meaning as defined above,
b. coupling of the activated carboxylic acid with a malonic acid derivative providing a β-ketoester precursor, in particular a β-ketoester precursor of the general formula 6a or 6b, as defined above
c. converting the β-ketoester precursor to the ketone of the general formula 1, in particular of the ketone of formula 1a or 1b, as defined above,
d. reduction of the ketone of the general formula 1, in particular reduction of the ketone of formula 1a or 1b, providing the alcohol of the general formula 5a to 5d.

According to a seventh aspect, the invention relates to an alcohol of a general formula 5a to 5d, as defined above, comprising a diastereochemical purity>98%.

According to a eight aspect, the invention relates to an alcohol of a general formula 5a to 5d, as defined above, producible by the process according to the sixth aspect of the invention, comprising a diastereochemical purity>98%.

According to a ninth aspect, the invention relates to a use of the chiral alcohol according to the seventh aspect of the invention or a preparation of a chiral ketone produced according to the sixth aspect of the invention in the production of d-nebivolol, l-Nebivolol or a mixture of d-nebivolol and l-Nebivolol, in particular a racemic mixture of d-nebivolol and l-Nebivolol, or the hydrochloride salts thereof.

According to a tenth aspect, the invention relates to a process for the preparation of d-nebivolol, l-Nebivolol or a mixture of d-nebivolol and l-Nebivolol, in particular a racemic mixture of d-nebivolol and l-Nebivolol, or the hydrochloride salts thereof
comprising the steps of:
a. activation of a carboxylic acid of a general formula 2, in particular of the formula 2a or 2b, by using a peptide coupling agent, with formula 2, 2a or 2b having the same meaning as defined above,
b. coupling of the activated carboxylic acid with a malonic acid derivative providing a β-ketoester precursor, in particular a β-ketoester precursor of the general formula 6a or 6b, as defined above
c. converting the β-ketoester precursor to the ketone of the general formula 1, in particular of the ketone of formula 1a or 1b, as defined above
d. reduction of the ketone of the general formula 1, in particular reduction of the ketone of formula 1a or 1b, providing a alcohol of the general formula 5a to 5d, as defined above,
e. provision of an protected aminoalcohol of the formula 7a to 7b,

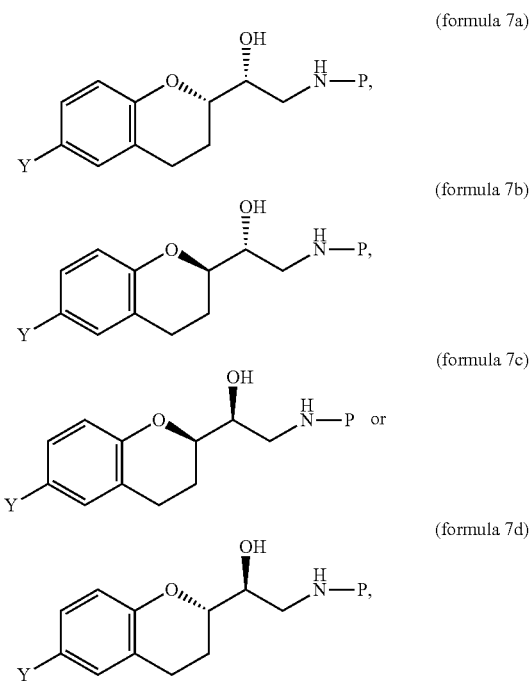

(formula 7a)

(formula 7b)

(formula 7c)

(formula 7d)

with Y having the same meaning as defined previously and P being an amine protecting group, derived form the alcohols of the general formula 5a to 5d,
f. coupling of the aminoalcohol 7a with the alcohol 5b or the aminoalcohol 7b with the alcohol 5a providing protected d-nebivolol, or coupling of the aminoalcohol 7c with the alcohol 5d or the aminoalcohol 7d with the alcohol 5c, providing protected l-nebivolol,
g. deprotection, providing d-nebivolol or l-Nebivolol, wherein optionally the d-nebivolol or l-nebivolol may be treated with hydrochloric acid, wherein further optionally the d-nebivolol or l-Nebivolol may be mixed providing a mixture of d-nebivolol or l-nebivolol, in particular a racemic mixture, prior to the treatment with hydrochloride acid.

As used herein the term "alkyl," refers to a saturated straight or branched hydrocarbon moiety containing up to 6, particularly up to 4 carbon atoms. Examples of alkyl groups include, without limitation, methyl, ethyl, propyl, butyl, n-hexyl, iso-propyl, iso-butyl or tert-butyl and the like. Alkyl groups typically include from 1 to about 6 carbon atoms ($C_1$ to $C_6$ alkyl).

As used herein the term "ee," refers to an enantiomeric excess of a substance. Enantiomeric excess is defined as the absolute difference between the enantiomers divided by the sum of the enatiomers and is expressed in percent. An analogue definition applies for a diastereomeric excess ("de"), also referred to as "diastereochemical purity".

A protecting group in the context of the present specification is a group employed to reduce the reactivity of a particular moiety. Protecting groups are well known to the person skilled in the art of organic chemistry. P. G. M. Wuts, "Greene's Protective Groups in Organic Synthesis," 4th ed. (2006, Wiley; ISBN 978-0-471-69754-1; 5th edition June 2013 Wiley-Blackwell).

The term "substituted" refers to the addition of a substituent group to a parent compound.

"Substituent groups" can be protected or unprotected and can be added to one available site or to many available sites in a parent compound. Substituent groups may also be further substituted with other substituent groups and may be attached directly or by a linking group such as an alkyl, an amide or hydrocarbyl group to a parent compound. "Substituent groups" amenable herein include, without limitation, halogen, oxygen, nitrogen, sulphur, hydroxyl, alkyl, alkenyl, alkynyl, acyl, carboxyl, aliphatic groups, alicyclic groups, alkoxy, substituted oxy, aryl, aralkyl, heterocyclic radical, heteroaryl, heteroarylalkyl, nitro or cyano.

DETAILED DESCRIPTION

It was evident from reactions in the racemic series (see example 1) that the preparation of chiral chloroketones via chiral acid chlorides and intermediate meldrumates is not suitable as this process resulted in substantial racemisation, partially induced by ketene formation from the acid chloride under the influence of bases. Various bases (e.g., pyridine, 2,6-lutidine, 2-chloropyridine, $Na_3PO_4$) and dosing regimes have been investigated to overcome these problems, but the results couldn't be improved.

These intrinsic problems with acid chlorides could not be overcome by using a formation of mixed anhydrides of 6-fluoro-chromanic acid and their conversion to chloroketones via known Meldrumate chemistry as it is illustrated below on the formation of the (S)-chloroketone (2-chloro-1-[(2S)-6-fluorochroman-2-yl]ethanone) from the chromane carboxylic acid ((2S)-6-fluorochromane-2-carboxylic acid) (scheme 3).

Scheme 3: Known Meldrumate chemistry route

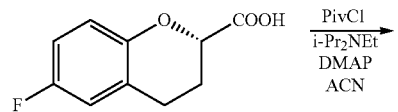

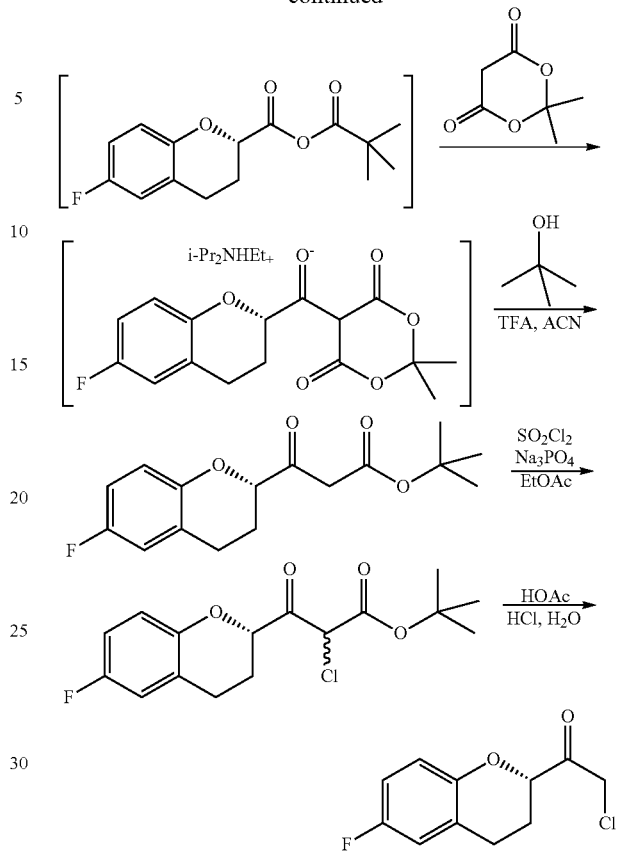

Although ketene formation could be avoided completely when using pivaloyl chloride for anhydride formation, however, now racemization of the enantiomerically pure chromanic acid anhydride occurred very quickly, even if only a small excess of base is present in the reaction mixture. Interestingly, the meldrumate once it has been formed is stable against strong bases like diisopropylethylamine, even if the base is applied in excess. Apparently, the reaction rate constant of (S)- or (R)-chromanic acid-anhydride formation is higher than the rate of its consumption by Meldrum's acid. Thus, the mixed anhydride accumulates and therefore undergoes partial racemization during its short life time under reaction conditions. In general, chiral chloroketones couldn't be obtained with ee>94% by that approach (see example 2).

These results could also not be improved by optimising the base (e.g. exchanging diisopropylethylamine against 4-(Dimethylamino)-pyridin (DMAP), 4-picoline, 2-chloro-pyridine and others). DMAP failed to give the mixed anhydride whereas 4-picoline and 2-chloro-pyridine were not superior regarding overall process yield and chiral purity. All attempts to improve the results by optimising the stoichiometry also failed. Replacement of pivaloyl chloride by ethyl chloroformate was also not effective.

Thus, all the known routes and variations thereof can not provide enantiomerically chloroketones in the necessary high purity. All reaction conditions using different bases as catalysts were accompanied by substantial racemisation at various steps of the overall process sequence.

The process according to the first aspect of the invention provides a solution to this problem. Surprisingly, the inventors found that peptide coupling agents like 1-Hydroxybenzotriazol (HOBt), Oximapure and carbonyldiimidazole (CDI) effected the conversion of FCA to the meldrumate without the need for a base.

A first aspect of the invention relates to a process for the preparation of a ketone of a general formula 1

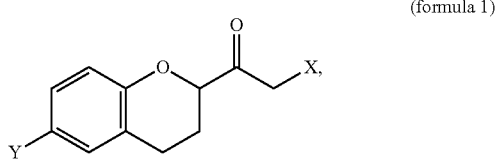

(formula 1)

with X being Cl or Br, in particular with X being Cl, with Y being F, Cl, Br, I or H, in particular with Y being F.

comprising the steps of:

a. activation of a carboxylic acid of a general formula 2

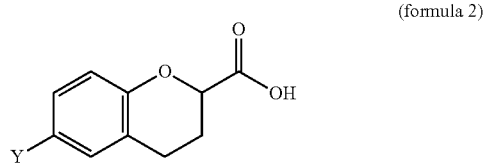

(formula 2)

by using a peptide coupling agent, with Y having the same meaning as defined above, b. coupling of the activated carboxylic acid with a malonic acid derivative providing a β-ketoester precursor, in particular a β-ketoester precursor of the general formula 6a or 6b,

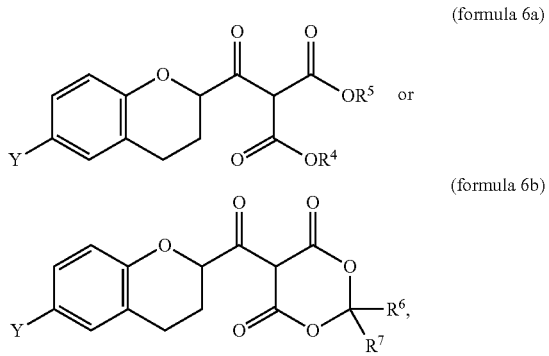

(formula 6a)

(formula 6b)

with $R^4$ being H or $C_1$ to $C_6$ alkyl, $R^5$ being $C_1$ to $C_6$ alkyl, $R^6$ being H or $C_1$ to $C_6$ alkyl and $R^7$ being $C_1$ to $C_6$ alkyl or a substituted or unsubstituted phenyl, in particular $R^6$ being $C_1$ to $C_3$ alkyl and $R^7$ being $C_1$ to $C_3$ alkyl c. converting the β-ketoester precursor to the ketone of the general formula 1.

The ketones of the general formula 1, in particular with X being Cl or Br and Y being F, are—either as a racemate or as enantiomerically pure compounds—useful intermediates in the preparation of nebivolol and its hydrochloride salt.

A general pathway is depicted in scheme 4 using the β-ketoester precursor of formula 6a as an example. Other β-ketoester precursor are also possible.

Scheme 4: General pathway of the first aspect of the invention:

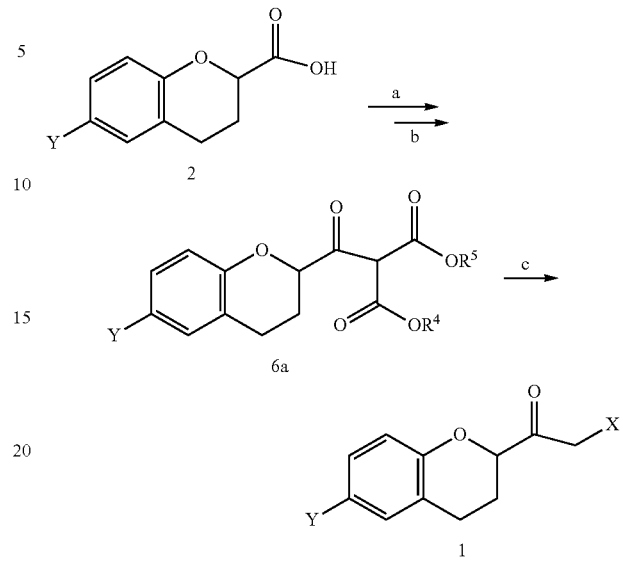

a) activation of a carboxylic acid 2 by using a peptide coupling agent;
b) coupling of the activated carboxylic acid with a malonic acid derivative providing a β-ketoester precursor (in this example 6a);
c) converting the β-ketoester precursor to the ketone 1.

As already discussed, there is a need to find a new method for providing ketones of formula 1. Surprisingly, the inventors found that peptide coupling agents allow a conversion of chromanic acid 2 to ketones 1 in a very high yield and purity. The use of peptide coupling agents allows a formation of the interim β-ketoester under neutral or even acidic conditions, thus, reducing the isomerisation substantially. Since the chemistry related to peptide coupling completely avoids the usage of bases it provides a solution to the above mentioned problems with respect to the substantial isomerisation occurring in the known routes.

In some embodiments, the malonic acid derivative of step b is a malonic diester of the formula $R^4$—O—C(=O)—$CH_2$—C(=O)—O—$R^{5'}$ with $R^4$ being a $C_1$ to $C_6$ alkyl and $R^5$ being a $C_1$ to $C_6$ alkyl, a malonic acid derivative of a formula 8

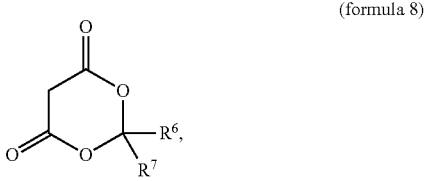

(formula 8)

with $R^6$ being $C_1$ to $C_6$ alkyl and $R^7$ being $C_1$ to $C_6$ alkyl, in particular $R^6$ and $R^7$ being $C_1$ to $C_3$ alkyl, more particularly $R^6$ and $R^7$ are $C_1$ alkyl (2,2-dimethyl-1,3-dioxane-4,6-dione; Meldrum's acid) or a malonic half ester of the formula $R^4$—O—C(=O)—$CH_2$—C(=O)—O—H or its Na— and Mg salts, with $R^4$ being a $C_1$ to $C_6$ alkyl.

In some embodiments, the malonic acid derivative of step b is a malonic diester of the formula $R^4$—O—C(=O)—$CH_2$—C(=O)—O—$R^5$, with $R^4$ being a $C_1$ to $C_6$ alkyl and $R^5$ being a $C_1$ to $C_6$ alkyl, providing the interim β-ketoester of the formula 6a by a coupling reaction with the activated carboxylic acid of step a.

In some embodiments, the malonic acid derivative of step b is a malonic diester the formula 8

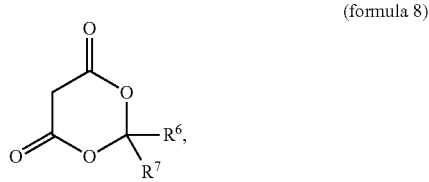
(formula 8)

with $R^6$ being $C_1$ to $C_6$ alkyl and $R^7$ being $C_1$ to $C_6$ alkyl, in particular the malonic acid derivative is 2,2-dimethyl-1,3-dioxane-4,6-dione (Meldrum's acid), providing the interim β-ketoester of the formula 5b by a coupling reaction with the activated carboxylic acid of step a.

In some embodiments, the malonic acid derivative of step b is a malonic half ester of the formula $R^4$—O—C(=O)—$CH_2$—C(=O)—O—H or its Na— and Mg salts, with $R^4$ being a $C_1$ to $C_6$ alkyl, providing the interim β-ketoester of the formula 6a by a coupling reaction with the activated carboxylic acid of step a.

In some embodiments, the activated carboxylic acid of step a is coupled with 2,2-dimethyl-1,3-dioxane-4,6-dione (Meldrums acid) providing the meldrumate of a general formula 3

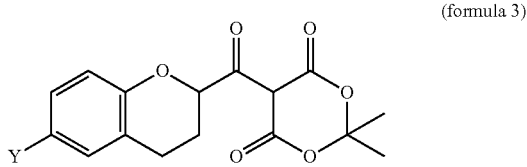
(formula 3)

as the β-ketoester precursor.

In some embodiments, the peptide coupling agent is selected from the group of, triazoles, carbonylimidazoles or imminoacetates, particular the peptide coupling agent is selected from the group of carbonylimidazoles.

In some embodiments, the peptide coupling agent is selected from the group of, 1-Hydroxybenzotriazol (HOBT), 1-Hydroxy-7-azabenzotriazol (HOAT), 1,1'-Carbonyldiimidazol (CDI), 1,1'-carbonylbis(3-methylimidazoliumtriflate) (CBMIT) or Ethylcyan(hydroxyimino)acetat (Oximapure®).

In some embodiments, the coupling of the activated carboxylic acid is achieved without the presence of a base additive.

The term "base additive" comprises a base according to the definition of Brønsted and Lowry ("proton acceptor"), which is added before the coupling step b of the carboxylic acid and the malonic acid derivative with the exception of peptide coupling agents. Thus, the base additive is present during the coupling reaction. The "base additive" may also be added before the coupling step in a previous reaction step. A "base additive" according to the invention encompasses any bases which are added to the reaction mixture for any reason, in particular for the activation of the carboxylic acid derivative or in support of said activation (e.g. Diisopropylethylamine, pyridine, 2,6-lutidine, 2-chloropyridine, $Na_3PO_4$). Bases (generally weak bases) which are generated during a reaction step (e.g. in the activation step with a peptide coupling agent) of the applied reagents (e.g. peptide coupling agents, malonic acid derivatives, carboxylic acids etc.) or as side reactions of said reagents or the described reagents are not considered as "bases additives" and, thus, not excluded during the reaction step.

It has to be noted that a peptide coupling agent, as specified previously, which might be defined according to the definition of Brønsted and Lowry ("proton acceptor"), is not considered as a "base additive" according to the invention, and thus, not excluded.

In some embodiments, the coupling of the activated carboxylic acid is achieved in a reaction mixture comprising a pH in the range of 8 or less, in particular a pH in the range of 7 or less.

In some embodiments, the β-ketoester precursor of formula 6b, in particular the meldrumate of the general formula 3, is converted to the ketone of the general formula 1 by using a β-ketoester of the general formula 4

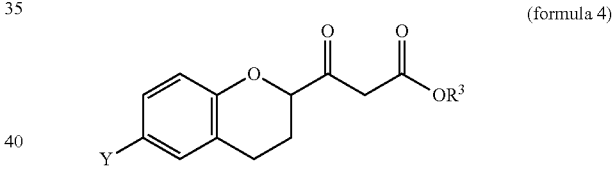
(formula 4)

as an intermediate, with Y having the same meaning as defined previously, wherein the compound of the general formula 4 is provided by alcoholysis of the β-ketoester precursor of the general formula 6b, in particular the meldrumate of the general formula 3, with an alcohol $R^3$OH, with $R^3$ being $C_1$-$C_6$ alkyl.

In some embodiments, the compound of the general formula 4 is halogenated, optionally hydrolyzed, and decarboxylized, to give the ketone of the general formula 1.

A general reaction pathway using a β-ketoester of the general formula 4 as an intermediate is depicted in Scheme 5.

Scheme 5:

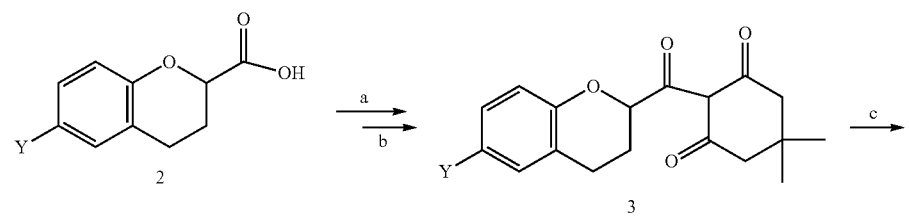

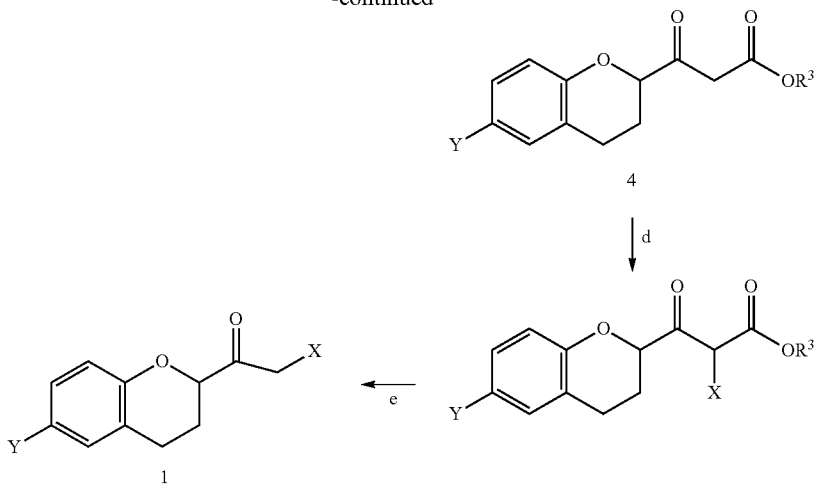

a) activation of a carboxylic acid 2 by using a peptide coupling agent;
b) coupling of the activated carboxylic acid with a Meldrum's acid providing meldrumate 3;
c) alkoholysis of the meldrumate 3 to the β-ketoester precursor 4;
d) halogenation of the β-ketoester precursor 4;
e) decarboxylation to the ketone 1.

In some embodiments, the β-ketoester precursor of formula 6a, in case the β-ketoester precursor derived from a reaction with a malonic half ester of the formula $R^4$—O—C(=O)—$CH_2$—C(=O)—O—H or its Na— and Mg salts, is decarboxylized to a β-ketoester of the general formula 4, subsequently halogenated and decarboxylized, to give the compound of the general formula 1, with $R^4$ having the same meaning as defined above.

In some embodiments, the chiral ketone of the general formula 1a or 1b

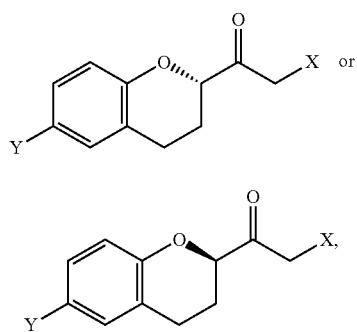

(formula 1a)

(formula 1b)

is provided by using the correspondent carboxylic acids of the general formula 2a or 2b

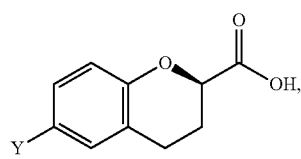

(formula 2a)

(formula 2b)

with X and Y having the same meaning as defined previously.

The same process steps and the same reaction conditions discussed with respect to the general formula 1 apply for providing a chiral ketone of the general formula 1a or 1b using the correspondent carboxylic acids of the general formula 2a or 2b.

It is understood that compounds depicted as a specific enantiomer or diastereomer (eg. formula 1a, 1b, 2a, 2b, 5a, 5b, 5c or 5d) and referred to as "pure" comprises said enantiomer or said diastereomer in a substantial excess, wherein the respective other possible enantiomers or diastereomers may be present in a very small amount. If not stated otherwise, said compounds comprise the highest purity possible, in which said compounds can be purchased, purified or synthesised.

The carboxylic acids of the general formula 2a or 2b is purchased in a purity of ee>99%.

In some embodiments, the preparation of the ketone of the general formula 1, 1a or 1b is carried out as an one-pot-approach without isolation of any intermediate.

A second aspect of the invention relates to a chiral ketone of the general formula 1a or 1b,

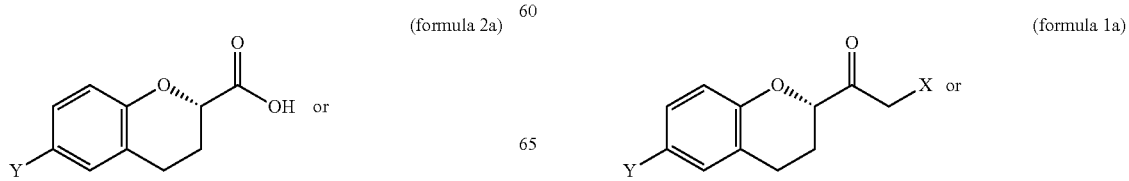

(formula 1a)

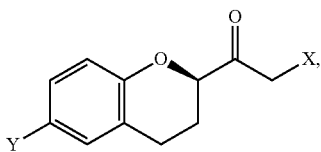
(formula 1b)

with X and Y having the same meaning as defined previously, comprising a purity of ee>98%.

A third aspect of the invention relates to a chiral ketone of the general formula 1a or 1b, as defined above, comprising a purity of ee>98%.

The chiral ketones of the general formula 1a or 1b comprises a very high purity (with respect to ee), which could not be obtained by the known processes. In general, chiral chloroketones couldn't be obtained with ee>94% (see example 2).

A fourth aspect of the invention relates to a use of a chiral ketone in the production of chiral alcohols of the general formula 5a to 5d, (formula 5a)

(formula 5b)

(formula 5c)

(formula 5d)

with X and Y having the same meaning as defined previously.

The use of the ketones 1a and 1b in a purity of ee>98% leads, after a reduction, in particular a stereospecific, enzymatic reduction, to the four chiral pure alcohols 5a to 5d with a diastereochemical purity of >98%.

A fifth aspect of the invention relates to a use of the chiral ketone in the production of d-nebivolol, l-Nebivolol or a mixture of d-nebivolol and l-Nebivolol, in particular a racemic mixture of d-nebivolol and l-Nebivolol, or the hydrochloride salts thereof.

The use of the ketones 1a and 1b as a starting material in a high purity (ee>98%) leads to the four chiral pure alcohols 5a to 5d in a high diastereochemical purity of >98%, which are further precursors in producing nebivolol. The use of starting materials and precursors in such a high purity leads to less unwanted side products (which also may be difficult to separate from the main product). Thus, providing d-nebivolol, l-Nebivolol, a mixture of d-nebivolol and l-Nebivolol or the hydrochloride salts thereof in a high yield and very high purity.

A sixth aspect of the invention relates to a process for the preparation of an alcohol of a general formula 5a to 5d, as defined above
comprising the steps of:
a. activation of a carboxylic acid of a general formula 2, in particular of the formula 2a or 2b, by using a peptide coupling agent, with formula 2, 2a or 2b having the same meaning as defined above,
b. coupling of the activated carboxylic acid of formula 2 with a malonic acid derivative, as defined above, providing a β-ketoester precursor, in particular a β-ketoester precursor of the general formula 6a or 6b, as defined above,
c. converting the β-ketoester precursor to the ketone of the general formula 1, in particular to the ketone of formula 1a or 1b, as defined above,
d. reduction of the ketone of the general formula 1, in particular of the ketone of formula 1a or 1b, providing the alcohol of the general formula 5a to 5d.

The reduction of the ketone of the general formula 1, in particular of the ketone of formula 1a or 1b, may be achieved by suitable standard reduction methods. The reduction of ketones to alcohols can be considered as basic knowledge of a person skilled in the art.

Particularly, a stereospecific, enzymatic reduction as disclosed in WO 2011/091968 A1 (in particular section [00028] to [00030], [00034] to [00039]) is applied, leading to the four chiral pure chloroalcohols 5a to 5d with a diastereochemical purity of >98%.

A seventh aspect of the invention relates to an alcohol of a general formula 5a to 5d, as defined above, comprising a diastereochemical purity of >98%.

An eight aspect of the invention relates to an alcohol of a general formula 5a to 5d, as defined above, producible by the process according to the sixth aspect of the invention, comprising a diastereochemical purity>98%.

A ninth aspect of the invention relates to a use of or a chiral alcohol in the production of d-nebivolol, l-Nebivolol or a mixture of d-nebivolol and l-Nebivolol, in particular a racemic mixture of d-nebivolol and l-Nebivolol, or the hydrochloride salts thereof.

The use of the four chiral pure alcohols 5a to 5d in a high diastereochemical purity of >98% as a precursor to Nebivolol provides less unwanted side products (which also may be difficult to separate from the main product). Thus, providing d-nebivolol, l-Nebivolol, a mixture of d-nebivolol and l-Nebivolol or the hydrochloride salts in a high yield and very high purity.

A tenth aspect of the invention relates to a process for the preparation of d-nebivolol, l-Nebivolol or a mixture of d-nebivolol and l-Nebivolol, in particular a racemic mixture of d-nebivolol and l-Nebivolol, or the hydrochloride salts thereof
comprising the steps of:
a. activation of a carboxylic acid of a general formula 2, in particular of the formula 2a or 2b, by using a peptide coupling agent, with formula 2, 2a or 2b having the same meaning as defined above,
b. coupling of the activated carboxylic acid of formula 2 with a malonic acid derivative, as defined above, providing a β-ketoester precursor, in particular a β-ketoester precursor of the general formula 6a or 6b, as defined above c. converting the β-ketoester precursor to the ketone of the general formula 1, in particular to the ketone of formula 1a or 1b, as defined above d. reduction of the ketone of the general formula 1, in particular of the ketone of formula 1a or 1b, providing an alcohol of the general formula 5a to 5d, as defined above, e. provision of an protected aminoalcohol of the formula 7a to 7b,

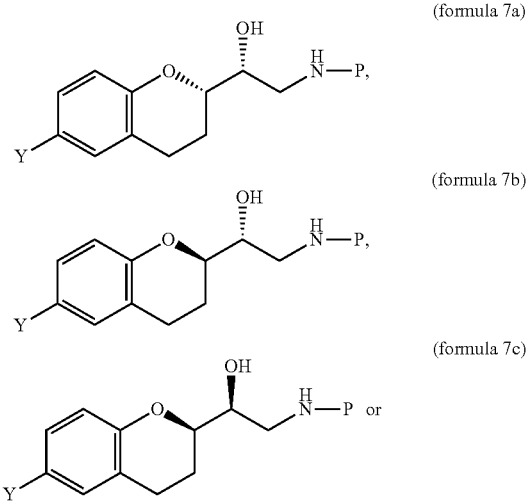

(formula 7a)

(formula 7b)

(formula 7c)

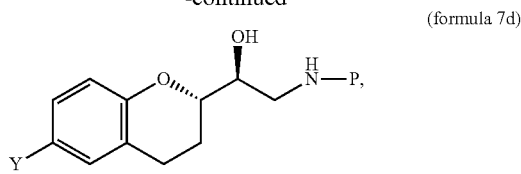

(formula 7d)

with Y having the same meaning as defined previously and P being an amine protecting group, wherein the protected aminoalcohol of the formula 7a to 7b is produced form the alcohols of the general formula 5a to 5d, f. coupling of the aminoalcohol 7a with the alcohol 5b or the aminoalcohol 7b with the alcohol 5a providing protected d-nebivolol, or coupling of the aminoalcohol 7c with the alcohol 5d or the aminoalcohol 7d with the alcohol 5c, providing protected l-nebivolol, g. deprotection, providing d-nebivolol or l-Nebivolol, wherein optionally the d-nebivolol or l-nebivolol may be treated with hydrochloric acid, wherein further optionally the d-nebivolol or l-Nebivolol may be mixed providing a mixture of d-nebivolol or l-nebivolol, in particular a racemic mixture, prior to said treatment with hydrochloride acid.

Concerning the steps d, e, f and g reference is made to the detailed description in the WO 2011/091968 A1 (in particular the examples 1 to 12 on page 15 to 21). The same conditions and reagents are applied in the above mentioned process of the tenth aspect of the invention.

Synthesis

The overall process for synthesis of pure ketones of formula 1a and 1b and alcohols of formula 5a to 5d, derived from the ketones of formula 1a and 1b, is shown, without being limited to it, in one example (Scheme 6)

Scheme 6 Example of the synthesis of pure chloroalcohols ("CLA") of formula 5a' to 5d' based on usage of either (R)- or (S)-6-fluoro-chromanic acid ("FCA") as starting material and CDI as activation reagent providing the chloroketones ("CLK") of formula 1a' and 1b' as intermediates. For a detailed description of the reaction conditions see examples 3 and 4.

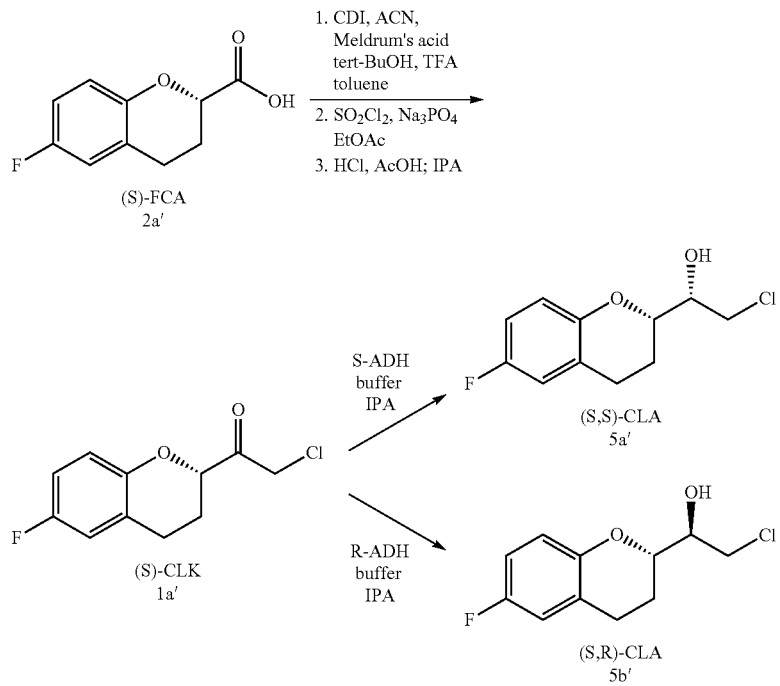

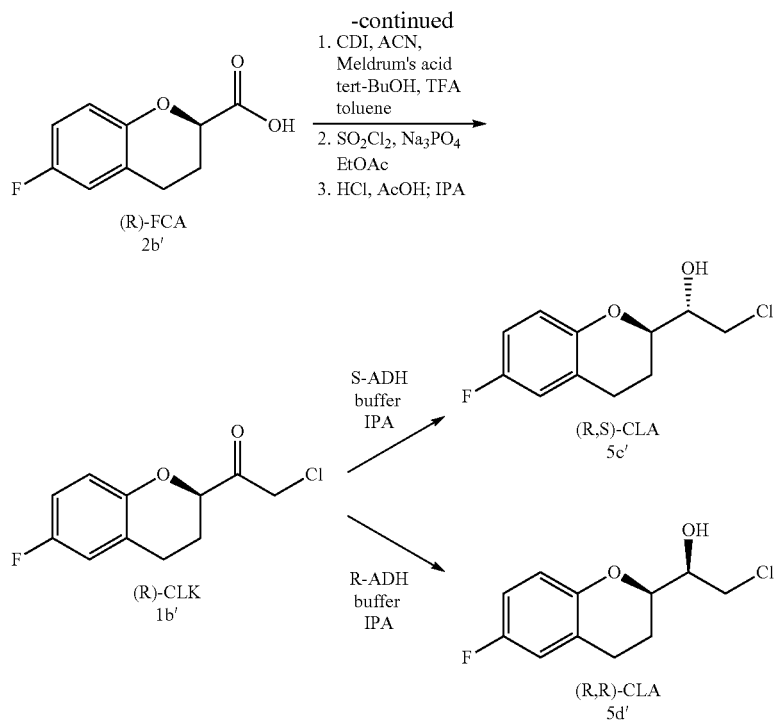

An analogue process applies for the use of chromanic acids of formula 2, 2a or 2b with Y being Cl, Br, I or H. The same applies for bromoketones of formula 1, 1a or 1b.

The activation of enantiomerically pure chromanic acids 2a' and 2b' (ee>99%) by CDI and its conversion to the meldrumate proceeds under mild conditions at ambient temperature. Extensive HPLC and GC analysis showed that there is no racemisation on this step. Meldrum's acid gives a clean reaction with the activated chromanic acid to afford the meldrumate quantitatively. The following acidic ring-opening with subsequent esterification to the final β-ketoester also proceeded without problems and didn't induce any racemisation (see EP 1803715 A1, in particular [0097] to [0110]). Conversion of the chiral ketoesters to chiral chloroketones 1a' and 1b' (and finally to chiral chloroalcohols 5a' to 5d') by first chlorination using $SO_2Cl_2$ followed by acid induced decarboxylation can be carried out as described in WO 2011/091968 A1, as discussed above concerning the reduction step, and EP 1803715 A1 section [0116] to [0119].

With the new process in hand it is possible to obtain (chloro)ketones of the formula 1a and 1b (respectively 1a' and 1b') with excellent purity (ee>98%). Overall yields of the conversion of chromanic acids to chiral (chloro)ketones are up to 80-85% which has to be considered as excellent for the whole sequence. Thus, this approach is a very effective one demonstrating its commercial and economical feasibility. Additional advantage can be taken from the fact that the synthesis of the (chloro)ketones can be carried out as one-pot process without isolation of all intermediates.

With the new optimised process in hand the final stereo-specific, enzymatic reduction of (S)- and (R)-chloroketones leads to the four chiral pure chloroalcohols using two different ADHs (alcoholdehydrogenase) with yields up to 99% and diastereochemical purity of >98%, respectively ee up to 99.8% (see scheme 7).

Scheme 7: Chiral pure chloroalcohols

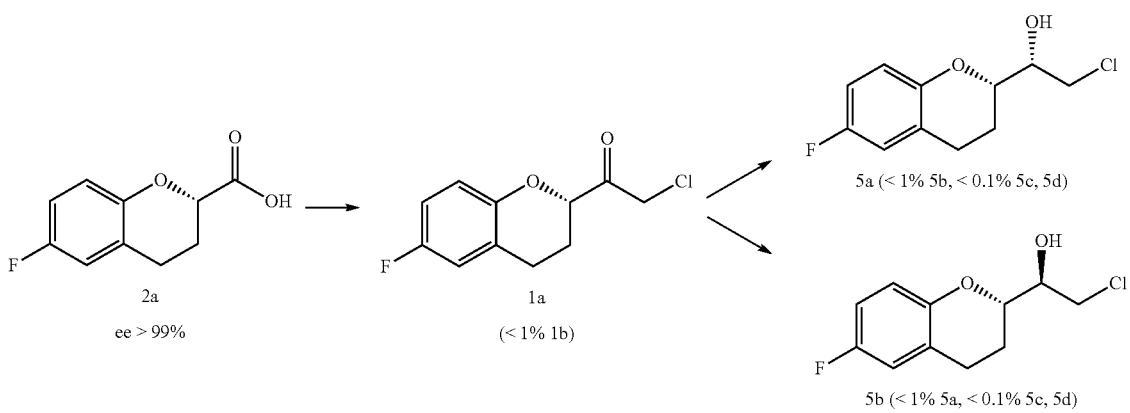

-continued

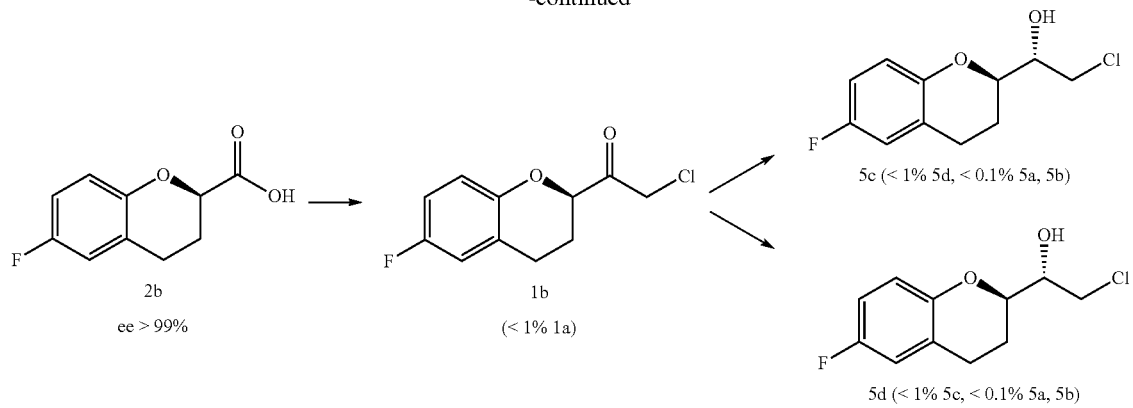

2b
ee > 99%

1b
(< 1% 1a)

5c (< 1% 5d, < 0.1% 5a, 5b)

5d (< 1% 5c, < 0.1% 5a, 5b)

EXAMPLES

Example 1 ent-Chloroketone Via Acid Chloride and Meldrumate 78 g (2S)-6-Fluorochromanic acid 2a (e.e. >99%) is dissolved in toluene (300 ml) and reacted with thionyl chloride (52.3 g) at 65-70° C. until complete conversion. The solvent is distilled off under vacuum. In a separate flask dichloromethane (260 ml) is charged followed by pyridine (61 ml) and Meldrum's acid (62 g). After cooling to 0-5° C. the previously prepared acid chloride is added over 3 hrs at 0° C. The resulting red brown slurry is stirred for additional 3h min at 20-25° C. After complete conversion 1M HCl is added (121 g) and the phases are separated. The organic phase is washed twice with 1M HCl (121 g) and finally washed twice with water (120 ml). The remaining organic phase is transferred to another flask containing tert. butanol (56 g). The mixture is heated to 70-80° C. for 6 h under continuous distillation of dichloromethane and acetone (CO2 evolvement) and normal pressure. After cooling to 55-60° C. tert. butanol is added again (53 g) and the reaction mixture heated again to 80° C. until no more distillate is observed. The mixture is chilled to 20-25° C. and 1M HCl (140 g) is added. The phases are separated and the organic phase is washed twice with sat. NaHCO$_3$ solution (148 g). The organic phase is concentrated under vacuum. The crude reaction product is transferred to a further flask and dissolved in ethyl acetate (500 ml). Na$_3$PO$_4$ (66 g) is added and the mixture cooled to 10-15° C. Sulfuryl chloride (61 g) is added slowly by keeping the temperature below 20° C. After complete conversion the mixture is treated with water (175 ml). The phases are separated and the organic phase treated again with water (70 ml). After phase separation the organic phase is concentrated in vacuum. The crude product is dissolved in ethyl acetate (40 ml) and mixed at ambient temperature with glacial acetic acid (291 ml) followed by 37% HCl (52 ml). The reaction mixture is heated to 40° C. for 3 h. After cooling to 20-25° C. toluene (140 ml) and water (100 ml) is added. The organic phase is washed twice with water (70 ml) and sat. NaHCO$_3$ solution (70 ml). After additional washing with water (70 ml) the organic phase is concentrated in vacuo. The resulting crude product is treated with isopropanol (165 ml) at 20-25° C. The mixture is stirred 2 h at 0-5° C. The product is filtered off and dried to give 1a' (36 g; e.e. 93.5%) as yellow crystals.

In an analogous manner (2R)-6-fluorochromanic acid 2b can be converted to chloroketone 1b'.

Example 2

Chloroketone Preparation with PivCl and Huenig Base (2S)-6-fluorochromanic acid (11.59 kg) 2a, Meldrum's acid (9.4 kg) and DMAP (0.6 kg) are dissolved in acetonitrile (33.7 l) at 20-25° C. N-ethyl diisopropylamine (16.7 kg) is added during 20 min at 20-25° C. Pivaloyl chloride (8.0 kg) is added to the clear yellow solution over 2 h. The solution is diluted with acetonitrile (6.2 l) and stirred for additional 4-5 h at 45-50° C. Tert. butanol (16.1 kg) is added, followed by trifluoroacetic acid (10.2 kg). The mixture is heated to 50-55° C. and stirred for additional 7 h. Solvents are distilled off under vacuum and the residue is dissolved in toluene (31.4 kg) after cooling to 20-25° C. Water (23 l) is added and the phases are separated. The organic phase is washed with sat. NaHCO$_3$ solution (23 l). The organic phase is washed again with water (23 l) and finally the solvents are distilled off to give the crude β-ketoester (19.0 kg). The product is transferred to a second vessel and dissolved in ethyl acetate (70.2 kg). Na$_3$PO$_4$ (9.7 kg) is added and the mixture cooled to 10° C. Sulfuryl chloride (9.0 kg) is dropped to the mixture during 2 h at 10° C. After complete conversion excess of sulfuryl chloride is hydrolysed with water (25.5 kg). The water phase is split off and discharged. The organic phase is washed with water (10.4 kg) and subsequently concentrated under vacuum to give 36.1 kg crude chlorinated β-ketoester. The crude material is treated with glacial acetic acid (42.8 kg) and 37% HCl (9.1 kg) at 20-25° C. and thereafter heated to 30-40° C. for about 7 h. After cooling to 20-25° C. toluene (17.8 kg) and water (20.4 kg) is added. After stirring for 30 min the phases are separated. The water phase is discharged and the organic phase washed twice with water (10.4 kg), sat. NaHCO$_3$ solution (11.0 kg) and finally with water (10.4 kg). The solvents are distilled off to yield a yellow-orange-oil. Isopropanol (38.0 kg) is added and half of the solvent is distilled off. The mixture is cooled to 0-5° C. and stirred 3 h. The precipitate is filtered off to give 6.86 kg 1a (50% of theoretical yield) of 95.8% purity (HPLC) and e.e. 96.2% (determined by chiral GC).

In a similar manner (2R)-6-fluorochromanic acid 2b (10.3 kg) is converted to 1b (6.1 kg) in 50.7% yield. Purity as determined by HPLC is 96.8% with e.e 93.2% (chiral GC).

Example 3

CDI-Process

CDI (100.7 kg) were charged in a vessel and suspended with acetonitrile (192 kg). A solution of (2R) 6-fluorochromanic acid 2a (110.7 kg) in acetonitrile (150 kg) was added over 45 min at 15-20° C. and stirred for additional 60 min until conversion has completed. A solution of Meldrum's acid (93.6 kg) in acetonitrile (97 kg) was added to the mixture at 15° C. After stirring for 12 h tert. butanol (169.5 kg) was added. The resulting mixture was cooled to 0-5° C. Trifluoroacetic acid (168 kg) was dropped to the mixture at 5° C. over 2 h and stirred for 6-7 h at 15-20° C. After complete conversion of the Meldrumate the solvent was removed by distillation. The resulting oily residue was dissolved in of toluene (279 kg) and washed with water (203 l), then twice with saturated aqueous $NaHCO_3$-solution (67 kg) and again with water (185 l). After phase separation, the aqueous layers were discarded and the toluene phase distilled off to give a slightly yellow oil which was azeotropically dried with toluene. The oily residue of (R)-FCA-β-ketoester in the reactor was dissolved in ethyl acetate (742 kg). $Na_3PO_4$ (92.5 kg) was added and the suspension transferred to a further vessel. Sulfurylchloride (87.6 kg) was added slowly at 0-5° C. over a period of 2 hours. The mixture was heated to 20° C. and stirred until completion of the reaction. Water (284 l) was added under stirring keeping the temperature below 15° C. After phase separation, the lower aqueous layer was discarded and the upper organic layer was washed water (138 l). The solvent was stripped under reduced pressure to give the (R)-FCA-α-chloro-β-ketoester as a yellow oily residue which was dissolved in glacial acetic acid (389.8 kg). Subsequently, 37% HCl (83.4 kg) was added and the mixture heated to 40° C. for 4 h. The mixture was cooled to 10° C. and 204 kg of sat. NaCl solution (204 kg) and toluene (162 kg) were added. After phase separation the organic phase was washed twice with brine (108 kg). The combined aqueous phases were re-extracted once with toluene (45 kg). Under vigorous stirring, saturated $NaHCO_3$-solution (65 l) was carefully added to the combined organic phase. After phase separation, the lower aqueous layer was discarded and the upper organic layer was washed twice with an aqueous solution of $Na_2SO_4$. Phases were separated and the organic phase concentrated under reduced pressure to yield an oily residue. Isopropanol (131 kg) was added and the residue dissolved at 40° C. A precipitate was obtained by cooling to 0° C. After additional stirring for 2 h the precipitate was filtered off. The filter cake was washed three times with ice-cold isopropanol and subsequently dried under reduced pressure. The mother liquor was reduced to the third part and crystallization was induced again by cooling to 0° C. The crystals were filtered off and both crops combined to yield 1b (92.45 kg; 71.6% of theoretical yield). Purity was 99% as determined by HPLC with e.e. 97.9% as determined by chiral GC.

Manufacturing of the corresponding (S)-chloroketone 1a was performed in the same manner.

Example 4

Conversion to Chloroalcohols (5a to 5d)

Preparation of the Buffer Solution for the Enzymatic Reduction:

Dissolve triethanolamine (4 g; 26.5 mmol) in water (215 ml). Adjust the pH of the solution, while stirring, to pH6.99 using 36% HCl (2.3 g). Add $ZnCl_2$ (0.057 g) and fill up to 270 ml. Then add glycerol (37.5 g) and mix well.

General Procedure for the Enzymatic Reduction:

Place isopropanol (20 g) in a flask and chill with ice to 0-5° C. Add β-NAD (10 mg) and then add pre-chilled buffer solution (10 ml). Subsequently, add 50 mmol of the chloroketone at 0° C. to the reaction mixture and finally add 6,000 units (S)- or (R)-selective alcohol dehydrogenase. Warm up the sample to 20-25° C. and stir for 24 h. After conversion is complete, centrifuge the reaction solution and extract with ethyl acetate (2×10 ml) after separating the phases. Wash the organic phases with sat. NaCl solution (20 ml) and then dry over $Na_2SO_4$. The raw product is obtained through removal of the solvent by distillation in vacuum.

(S)-2-chloro-1-((R)-6-fluoro-3,4-dihydro-2H-chromen-2-yl)-ethanol 5b'

(2S)-6-Fluorochronnan-2-yl-2-chloroethan-1-one 1a' and (R)-selective alcohol dehydrogenase were used in accordance with the specifications provided above to obtain 11.42 g (99% theoretical yield) 5b' (d.e. 98.3%; e.e. 99.8%).

LC-MS: m/z=230.232 (MH+, 100%)

(R)-2-chloro-1-((R)-6-fluoro-3,4-dihydro-2H-chromen-2-yl)-ethanol 5d'

In analogous manner (2R)-6-Fluorochroman-2-yl-2-chloroethan-1-one 1b' and (R)-selective alcohol dehydrogenase were used to obtain 11.07 g (96% of theoretical yield) 5d' (d.e. 97.9%; e.e. 99.8%)

LC-MS: m/z=230.232 (MH+, 100%)

(R)-2-chloro-1-((S)-6-fluoro-3,4-dihydro-2H-chromen-2-yl)-ethanol 5c'

In analogous manner (2R)-6-Fluorochroman-2-yl-2-chloroethan-1-one 1b' and (S)-selective alcohol dehydrogenase were used to obtain 11.42 g (99% of theoretical yield) 5c' (d.e. 98.0%; e.e. 99.8%)

LC-MS: m/z=230.232 (MH+, 100%)

(S)-2-chloro-1-((S)-6-fluoro-3,4-dihydro-2H-chromen-2-yl)-ethanol 5a'

In analogous manner (2S)-6-Fluorochroman-2-yl-2-chloroethan-1-one 1a' and (S)-selective alcohol dehydrogenase were used to obtain 10.72 g (93% of theoretical yield) 5a' (d.e. 98.1%; e.e. 99.9%)

LC-MS: m/z=230.232 (MH+, 100%)

The invention claimed is:

1. A process for the preparation of a ketone of a general formula 1

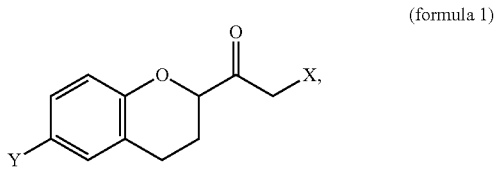

(formula 1)

with X being Cl or Br,
comprising the steps of:
a. reacting a carboxylic acid of a general formula 2

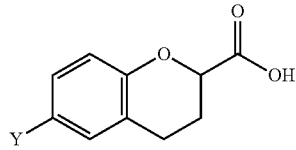

(formula 2)

with carbonyldiimidazole to yield an activated carboxylic acid,
b. reacting the activated carboxylic acid with a malonic acid derivative, wherein no base additive is present, yielding a β-ketoester precursor of the general formula 6a or 6b,

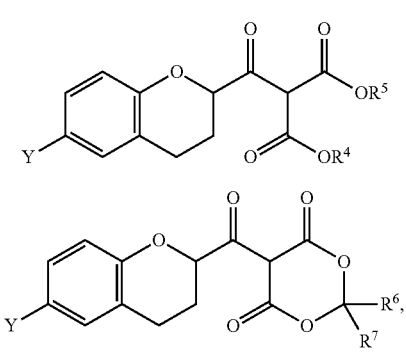

(formula 6a)

(formula 6b)

c. converting the β-ketoester precursor to the ketone of the general formula 1, wherein $R^4$ and $R^6$ independently of one another are H or $C_1$ to $C_6$ alkyl, $R^5$ is $C_1$ to $C_6$ alkyl, $R^7$ is $C_1$ to $C_6$ alkyl or a substituted or unsubstituted phenyl, and Y is F, Cl, Br, I or H.

2. The process according to claim 1, wherein the malonic acid derivative is
a malonic diester of the formula $R^{4a}$—O—C(=O)—$CH_2$—C(=O)—O—$R^5$, or
a malonic acid derivative of a formula 8

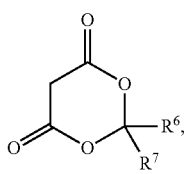

(formula 8)

or
a malonic half ester of the formula $R^{4b}$—O—C(=O)—$CH_2$—C(=O)—O—H or its Na— and Mg salts, with $R^{4b}$ being a $C_1$ to $C_6$ alkyl,
wherein $R^{4a}$ is a $C_1$ to $C_6$ alkyl and $R^5$ is a $C_1$ to $C_6$ alkyl, $R^6$ is $C_1$ to $C_6$ alkyl and $R^7$ is $C_1$ to $C_6$ alkyl or a substituted or unsubstituted phenyl.

3. The process according to claim 1, wherein the activated carboxylic acid of step a is coupled with 2,2-dimethyl-1,3-dioxane-4,6-dione (Meldrum's acid) providing the meldrumate of a general formula 3

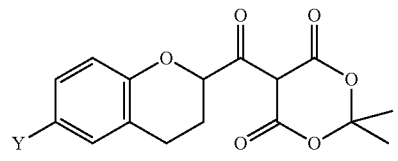

(formula 3)

as the β-ketoester precursor.

4. The process according to claim 1, wherein the step a is conducted in a reaction mixture comprising a pH in the range of 8 or less.

5. The process according to claim 3, wherein the meldrumate of general formula 3 is converted to the ketone of the general formula 1 wherein a β-ketoester of the general formula 4

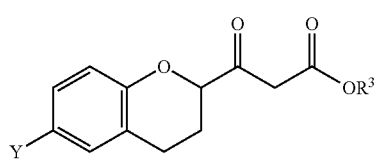

(formula 4)

is an intermediate, and wherein $R^3$ is $C_1$-$C_6$ alkyl.

6. The process according to claim 5, wherein the compound of the general formula 4 is halogenated, optionally hydrolyzed, and decarboxylated, to give the ketone of the general formula 1.

7. The process according to claim 1, wherein
the β-ketoester precursor of formula 6a, in case the β-ketoester precursor derived from a reaction with a malonic half ester of the formula $R^4$—O—C(=O)—$CH_2$—C(=O)—O—H or its Na— and Mg salts, is decarboxylized to a β-ketoester of general formula 4,

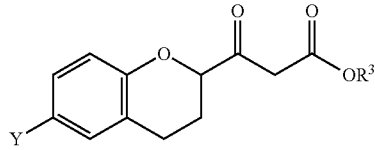

(formula 4)

subsequently halogenated and decarboxylated, to give the ketone of the general formula 1,
with $R^4$ having the same meaning as defined above.

8. The process according claim 1, wherein the chiral ketone of the general formula 1a or 1b

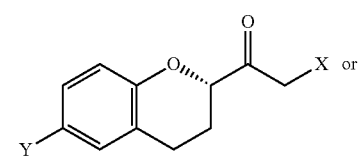

(formula 1a)

-continued
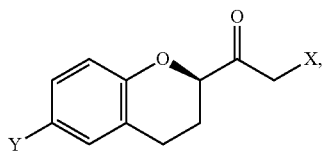
(formula 1b)
is provided by using the correspondent carboxylic acids of the general formula 2a or 2b
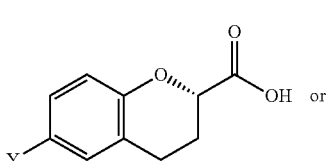
(formula 2a)
or
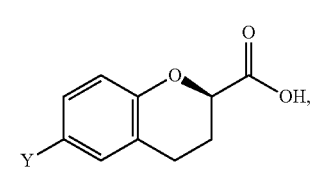
(formula 2b)
with X and Y having the same meaning as defined previously.
* * * * *